(12) United States Patent
Milijasevic et al.

(10) Patent No.: US 9,008,795 B2
(45) Date of Patent: Apr. 14, 2015

(54) CATHETER HANDLE ASSEMBLY

(75) Inventors: Zoran Milijasevic, Bayview (AU);
David Ogle, Cowan (AU)

(73) Assignee: Cathrx Ltd, Homebush Bay (AU)

( * ) Notice: Subject to any disclaimer, the term of this patent is extended or adjusted under 35 U.S.C. 154(b) by 1474 days.

(21) Appl. No.: 12/375,867

(22) PCT Filed: Aug. 2, 2007

(86) PCT No.: PCT/AU2007/001081
§ 371 (c)(1),
(2), (4) Date: Jan. 7, 2010

(87) PCT Pub. No.: WO2008/014557
PCT Pub. Date: Feb. 7, 2008

(65) Prior Publication Data
US 2010/0137955 A1    Jun. 3, 2010

Related U.S. Application Data

(60) Provisional application No. 60/835,501, filed on Aug. 4, 2006.

(51) Int. Cl.
A61N 1/375        (2006.01)
A61M 25/00       (2006.01)
A61B 18/14        (2006.01)
A61M 25/01       (2006.01)

(52) U.S. Cl.
CPC ........ *A61M 25/0009* (2013.01); *A61B 18/1492* (2013.01); *A61M 25/0136* (2013.01)

(58) Field of Classification Search
CPC .......................... A61B 1/00066; A61B 1/0052
USPC .............................. 607/116; 604/264; 606/147
See application file for complete search history.

(56) References Cited

U.S. PATENT DOCUMENTS

| 3,847,140 A | 11/1974 | Ayella |
| 4,940,064 A | 7/1990 | Desai |
| 5,117,839 A | 6/1992 | Dance |

(Continued)

FOREIGN PATENT DOCUMENTS

| EP | 0 962 191 A1 | 12/1991 |
| EP | 0 962 191 B1 | 12/1991 |

(Continued)

OTHER PUBLICATIONS

Written Opinion of the International Search Authority, mailed Oct. 4, 2007, for PCT/AU2007/001081, filed on Aug. 2, 2007, 5 pages.

(Continued)

*Primary Examiner* — Christopher D Koharski
*Assistant Examiner* — Natasha Patel
(74) *Attorney, Agent, or Firm* — TraskBritt

(57) ABSTRACT

A catheter handle assembly includes a holder having a proximal end and a distal end. An electrode sheath carrier is arranged at the distal end of the holder. A shape imparting element carrier is removably mountable to the proximal end of the holder, the shape imparting element carrier having at least one mounting formation for mounting at least a part of a shape imparting element. A slide is displaceably arranged in the holder with a distal end of the slide mounting the electrode sheath carrier and a proximal end of the slide terminating in proximity to the shape imparting element carrier.

15 Claims, 4 Drawing Sheets

(56) References Cited

U.S. PATENT DOCUMENTS

| | | |
|---|---|---|
| 5,170,787 A | 12/1992 | Lindegren |
| 5,190,050 A | 3/1993 | Nitzsche |
| 5,327,905 A | 7/1994 | Avitall |
| 5,441,504 A * | 8/1995 | Pohndorf et al. ............ 606/129 |
| 5,487,757 A | 1/1996 | Truckai et al. |
| 5,617,854 A | 4/1997 | Munsif |
| 5,634,881 A | 6/1997 | Francis |
| 5,656,029 A | 8/1997 | Imran et al. |
| 5,656,030 A | 8/1997 | Hunjan et al. |
| 5,662,119 A | 9/1997 | Brennen et al. |
| 5,674,271 A | 10/1997 | Denker |
| 5,722,403 A * | 3/1998 | McGee et al. ............... 600/373 |
| 5,882,333 A | 3/1999 | Schaer et al. |
| 5,941,817 A | 8/1999 | Crawford |
| 5,987,344 A | 11/1999 | West |
| 5,997,526 A | 12/1999 | Giba et al. |
| 6,059,739 A * | 5/2000 | Baumann ..................... 600/585 |
| 6,102,926 A | 8/2000 | Tartaglia et al. |
| 6,126,657 A | 10/2000 | Edwards et al. |
| 6,217,574 B1 | 4/2001 | Webster |
| 6,221,070 B1 | 4/2001 | Tu et al. |
| 6,251,092 B1 | 6/2001 | Qin et al. |
| 6,332,880 B1 | 12/2001 | Yang et al. |
| 6,611,710 B2 | 8/2003 | Gomperz et al. |
| 7,551,968 B2 | 6/2009 | Flach et al. |
| 7,947,000 B2 * | 5/2011 | Vargas et al. ................ 600/587 |
| 2003/0014037 A1 * | 1/2003 | Thompson et al. .......... 604/528 |
| 2003/0130620 A1 | 7/2003 | Alokaili |
| 2003/0135230 A1 * | 7/2003 | Massey et al. ............... 606/190 |
| 2003/0139794 A1 | 7/2003 | Jenney et al. |
| 2003/0181855 A1 | 9/2003 | Simpson et al. |
| 2003/0216711 A1 | 11/2003 | Rabiner et al. |
| 2004/0127915 A1 | 7/2004 | Fleenor et al. |
| 2005/0060885 A1 | 3/2005 | Johnson et al. |
| 2005/0085883 A1 * | 4/2005 | Ollivier et al. ............... 607/116 |
| 2005/0182387 A1 | 8/2005 | Webler |
| 2006/0142694 A1 | 6/2006 | Bednarek et al. |
| 2006/0168805 A1 | 8/2006 | Hegland et al. |
| 2008/0045921 A1 | 2/2008 | Anderson et al. |

FOREIGN PATENT DOCUMENTS

| | | |
|---|---|---|
| EP | 0 898 940 A1 | 3/1999 |
| EP | 0 980 693 A1 | 2/2000 |
| EP | 0 980 693 B1 | 2/2000 |
| EP | 0 982 047 A2 | 3/2000 |
| EP | 0 982 047 A3 | 3/2000 |
| EP | 0 982 047 B1 | 3/2000 |
| EP | 1400208 A1 | 3/2004 |
| EP | 1512427 A2 | 3/2005 |
| EP | 1618917 A2 | 1/2006 |
| WO | 9802201 | 1/1998 |
| WO | 9956810 | 11/1999 |
| WO | 0137723 | 5/2001 |
| WO | 0232497 | 4/2002 |
| WO | WO-2004/039273 A2 | 5/2004 |
| WO | WO-2004/039273 A3 | 5/2004 |
| WO | 2004100813 A2 | 11/2004 |
| WO | 2005051216 A1 | 6/2005 |
| WO | 2005070491 A2 | 8/2005 |
| WO | 2005094661 A1 | 10/2005 |
| WO | 2006012668 A1 | 2/2006 |
| WO | 2006012671 A1 | 2/2006 |
| WO | 2006092016 A1 | 9/2006 |
| WO | WO-2006/135988 A1 | 12/2006 |

OTHER PUBLICATIONS

International Preliminary Report on Patentability, mailed Feb. 10, 2009, for PCT/AU2007/001081, filed on Aug. 2, 2007, 6 pages.
Australian Examination Report for AU Application No. 2007281031, dated Nov. 22, 2011, 2 pages.
European Search Opinion for EP Application No. 07784723.4, filed Aug. 2, 2007, 1 page.
U.S. Appl. No. 60/798,254, filed May 5, 2006, for Milijasevic et al.
U.S. Appl. No. 60/835,501, filed Aug. 4, 2006, for Milijasevic et al.
International Search Report mailed on Oct. 4, 2007, for PCT/AU2007/001081, filed on Aug. 2, 2007, five pages.
Supplemental European Search Report mailed on Nov. 19, 2009, for EP Application No. 07784723.4, filed on Aug. 2, 2007, three pages.
European Search Report dated Aug. 21, 2013, for EP Application No. 13166897, filed May 5, 2006, 11 pages.

* cited by examiner

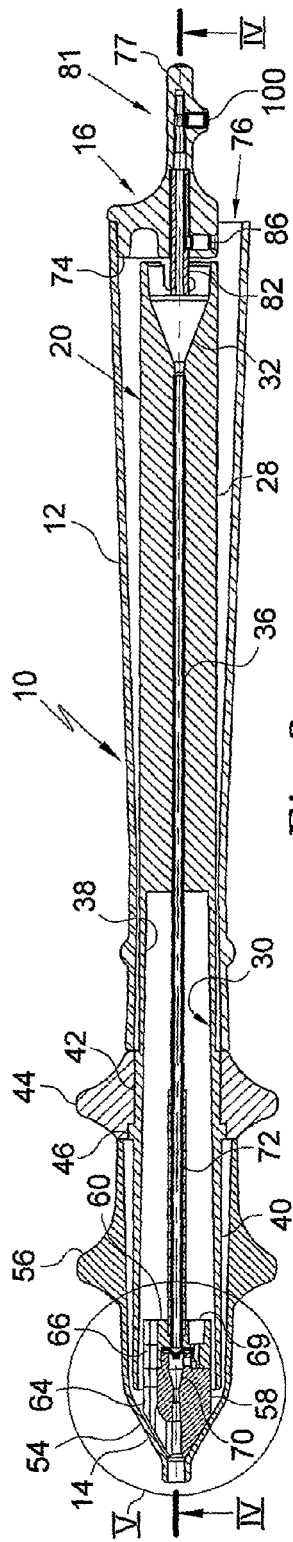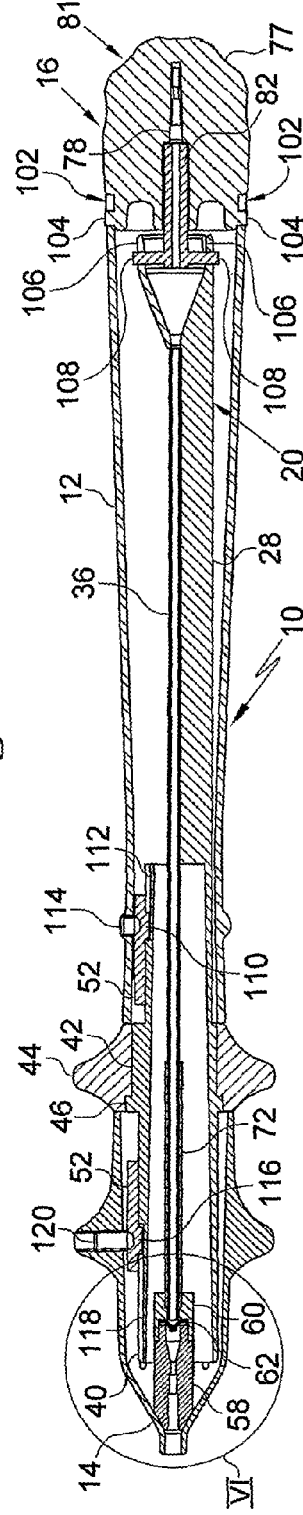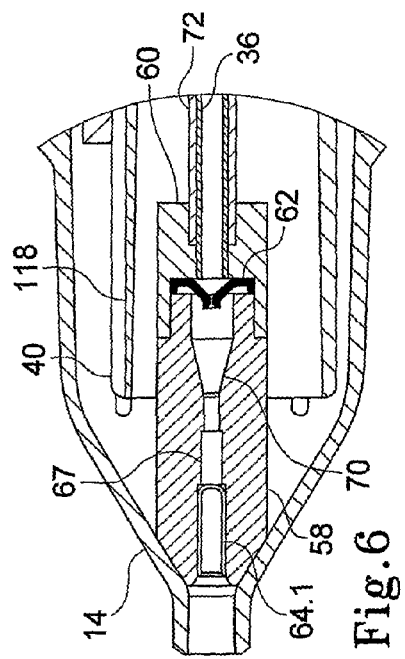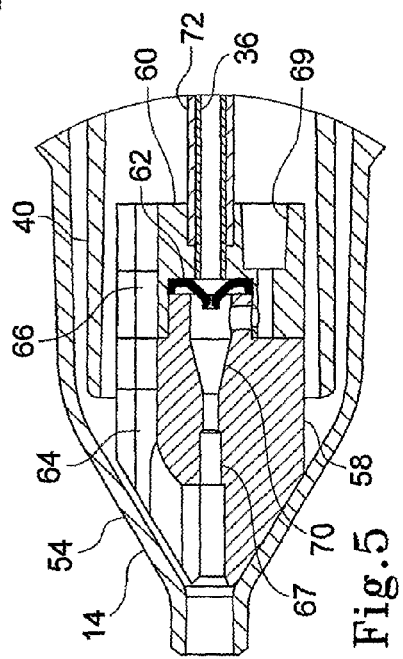

CATHETER HANDLE ASSEMBLY

CROSS-REFERENCE TO RELATED APPLICATIONS

The present application is a National Phase filing under 35 U.S.C. §371 of International Application No. PCT/AU2007/001081, filed on Aug. 2, 2007, which claims the benefit of U.S. Provisional Patent Application No. 60/835,501, filed on Aug. 4, 2006, the contents of each of which is hereby incorporated herein in its entirety by this reference. The subject matter of the present application is related to U.S. patent application Ser. No. 12/299,117, filed Aug. 3, 2009, pending.

FIELD

This invention relates, generally, to catheters and, more particularly, to a modular catheter assembly, to a catheter handle assembly and to components for a modular catheter assembly.

BACKGROUND

Catheters, such as those used in cardiovascular applications, are comprised of an elongate electrode carrying element mounted on a distal end of a handle. The handle has at least one connector so that a patient cable can be connected to a proximal end of the handle to feed signals through the handle to the electrodes. Often, these catheters include steering mechanisms or stylets arranged within the electrode carrying element to effect steering of a distal end of the electrode carrying element.

Such an arrangement results in an expensive piece of equipment, particularly the handle, which has the at least one connector and cabling. Also, because of voids in the electrode carrying element and in the interior of the handle, it is not possible, generally, to effect sufficient sterilization of such catheters to allow them to be reused. Thus, in most cases, the catheters are used once only and are then disposed of.

Not only does this create a substantial expense but there is the environmental problem of disposal of potentially hazardous items.

SUMMARY

According to one aspect of the invention, there is provided a catheter handle assembly, which includes:
  a holder having a proximal end and a distal end;
  an electrode sheath carrier arranged at the distal end of the holder;
  a shape imparting element carrier removably mountable to the proximal end of the holder, the shape imparting element carrier having at least one mounting formation for mounting at least a part of a shape imparting element; and
  a slide displaceably arranged in the holder with a distal end of the slide mounting the electrode sheath carrier and a proximal end of the slide terminating in proximity to the shape imparting element carrier.

The holder may taper inwardly from its proximal end to its distal end. An abutment may be arranged on the holder to provide purchase for a user's hand. This arrangement improves the balance and the ergonomics of the handle assembly.

The shape imparting element carrier may comprise a manipulating element and a receiving member, for receiving a further part of the shape imparting element, slidably received in an end of the manipulating element. Further, the manipulating element and the receiving member may include locating formations receivable in complementary receiving formations of the holder and the slide, respectively. The locating formations and receiving formations may be complementary bayonet-type fittings.

Preferably, the slide includes a guide arrangement arranged in proximity to its receiving formation, the guide arrangement guiding the shape imparting element into a proximal end of the slide. The guide arrangement may be in the form of a funnel-shaped member for guiding the shape imparting element into the slide.

The slide may include a body member which supports a guide member extending distally from the guide arrangement. The guide member may be a primary guide tube supported by the body.

A secondary guide member may extend proximally from the electrode sheath carrier, the secondary guide member cooperating with the guide member of the slide for guiding and supporting the shape imparting element in the holder. Likewise, the secondary guide member may be a secondary guide tube that is slidably received over the primary guide tube.

A distal part of the body member may be tubular and may project from a distal end of the holder, the electrode sheath carrier being slidably received on a distal portion of the tubular part. With this arrangement, the electrode sheath carried, in use, by the electrode sheath carrier can be extended and retracted relative to the shape imparting element received in a lumen of the electrode sheath. Thus, a distal end of the electrode sheath, the distal end carrying electrodes, can be manipulated by the clinician to be inserted into difficult to reach sites in a patient's body and/or to enhance tissue/electrode contact.

The tubular part may include a proximal portion arranged in the distal end of the holder, the proximal portion being separated from the distal portion by a mount, a slide control member being carried by the mount. For ease of molding, the slide control member may be a separate element which is a tight fit on the mount.

The proximal portion and the distal portion of the tubular part may each carry a friction-inducing component for increasing friction between the slide and the holder and between the slide and the electrode sheath carrier, respectively. The friction-inducing components may be friction pads carried on opposed sides of the mount.

The electrode sheath carrier may carry an adaptor which facilitates the insertion of the shape imparting element through the electrode sheath carrier. Further, the electrode sheath carrier may include an adaptor carrying a closure element for inhibiting backflow of fluid into the holder.

The manipulating element may have a substantially paddle-shaped handle projecting axially from the holder. A proximal end of the holder and the manipulating element may define an access opening through which at least one of a bundle of electrical conductors and a conduit can pass.

According to a second aspect of the invention, there is provided an electrical lead, which includes:
  a lumen defining member, the lumen defining member having a discontinuity along its length to create a proximal part and a distal part;
  a plurality of conductors carried on an outer surface of the lumen defining member, the conductors being separated from the lumen defining member at the discontinuity to enable access to be gained to a part of the lumen defined by the distal part, the plurality of conductors electrically bridging the discontinuity; and at least one electrode carried on the distal part of the lumen defining member.

The electrical lead may be intended for use with the catheter handle assembly as described above, a proximal end of the distal part being secured to a distal end of the electrode sheath carrier, the electrode sheath carrier defining a passage through which the proximal part of the lumen defining member and a bundle of the conductors pass to extend internally within the holder and to exit through the proximal end of the holder.

BRIEF DESCRIPTION OF THE DRAWINGS

FIG. 3 shows a sectional plan view of the handle assembly;

FIG. 4 shows a sectional side view of the handle assembly taken along line IV-IV in FIG. 3;

FIG. 5 shows, on an enlarged scale, the encircled part of FIG. 3;

FIG. 6 shows, on an enlarged scale, the encircled part of FIG. 4;

DETAILED DESCRIPTION

Figure 2:
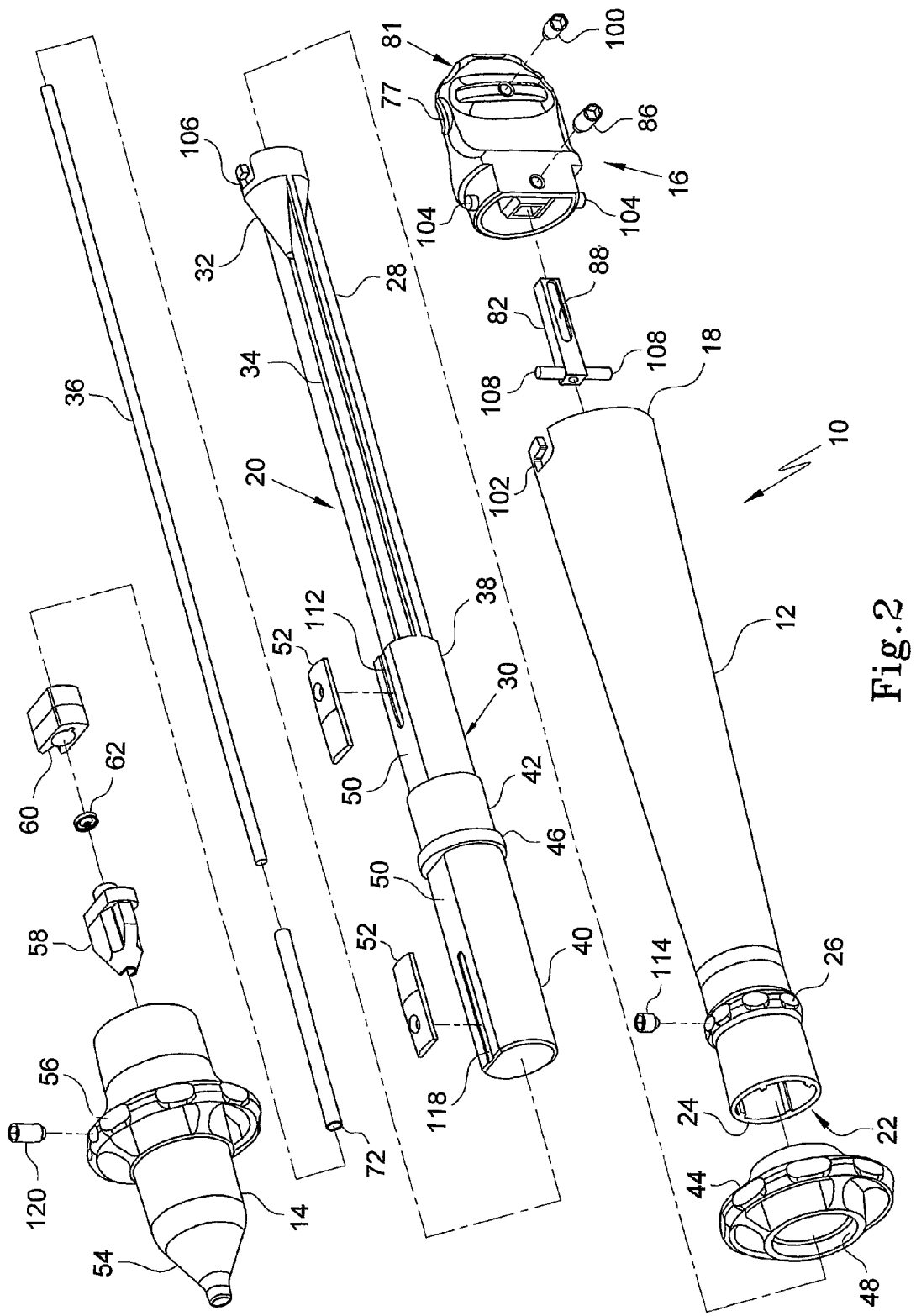
FIG. 2 shows a three-dimensional, exploded view of the handle assembly.

In the drawings, reference numeral 10 generally designates a catheter handle assembly, in accordance with an embodiment of the invention. The handle assembly 10 includes a tubular holder 12. An electrode sheath carrier 14 is mounted distally of the holder 12. A shape imparting element carrier or knob 16 is arranged at a proximal end 18 of the holder 12. A slide 20 (FIGS. 2 to 4) is received within an interior 22 of the holder 12.

The holder 12 tapers inwardly from its proximal end 18 to a distal end 24. An abutment 26 is arranged on the holder 12 proximally of the distal end 24 of the holder 12 to provide purchase for a clinician's hand when manipulating the handle assembly 10. The tapered nature of the holder 12 and the abutment 26 provide a balanced handle assembly 10 which facilitates manipulation by the clinician.

The slide 20 comprises a body member 28 terminating in an enlarged, tubular part 30. A guide mechanism in the form of a funnel-shaped member 32 is arranged at a proximal end of the body member 28. The funnel-shaped member 32 assists in inserting a shape imparting element (not shown) into the proximal end of the slide 20.

The body member 28 has a longitudinally extending, centrally located slot 34 extending from the funnel-shaped member 32. A metal tube 36, which acts as a primary guide tube, is received in the slot 34 and is secured in position, for example, by an appropriate adhesive. The tube 36 projects into the tubular portion 30 as shown in greater detail in FIGS. 3 and 4 of the drawings.

The enlarged, tubular part 30 of the body member 28 has a proximal portion 38 and a distal portion 40 separated by a radially raised mount 42. The mount 42 and the distal portion 40 of the tubular part 30 of the slide 20 project from the distal end 24 of the holder 12. A slide control member 44 is mounted on the mount 42. For ease of molding, the slide control member 44 is removably mounted on the mount 42 and is adhered in position. It will, however, be appreciated that, with suitable molding techniques, the slide control member 44 could be molded with the body member 28 as a one-piece molding.

A distal end of the mount 42 defines an annular locating rib 46 which is received in a complementary annular groove 48 of the slide control member 44. This serves to locate the slide control member 44 relative to the mount 42.

It is also to be noted that the tubular part 30 of the slide 20 has flats 50 defined on both the proximal portion 38 and the distal portion 40. The flats 50 carry friction-inducing components in the form of friction pads 52. The proximal friction pad 52 induces friction between the slide 20 and the interior 22 of the holder 12 and the distal friction pad 52 induces friction between the slide 20 and the electrode sheath carrier 14.

The electrode sheath carrier 14 comprises a nose cone-like element 54 which has a control member 56 formed integrally therewith as a one-piece unit. The electrode sheath carrier 14 is slidably mounted on the distal portion 40 of the tubular part 30 of the slide 20. With this arrangement, the electrode sheath carrier 14 can be displaced axially with respect to the remainder of the holder 12. This allows an electrode sheath (not shown) carried by the electrode sheath carrier 14 to be displaced relative to a shape imparting element received in a lumen of the electrode sheath. The electrode sheath is manufactured according to the Applicant's manufacturing technique as described in the Applicant's International Patent Application Number PCT/AU01/01339, dated Oct. 19, 2001 and titled "An Electrical Lead". A benefit of the manufacturing technique is that an electrode sheath results having an unimpeded lumen. This results from the conductors for electrodes of the electrode sheath being helically wound about an outer surface of a lumen defining component of the electrical lead. In other words, the conductors do not extend through the lumen of the electrical lead. The shape imparting element can therefore be inserted into the lumen of the electrode sheath via the electrode sheath carrier.

A frustoconical guide member 58 is received within the electrode sheath carrier 14 to guide insertion of the shape imparting element through the electrode sheath carrier 14.

An adaptor 60 is, optionally, secured to a proximal end of the guide member 58. The adaptor 60 is used when a catheter with which the handle assembly 10 is used includes irrigation. Thus, the adaptor 60 mounts a closure member in the form of a membrane 62. The membrane 62 is pierced by the shape imparting element when it is inserted through the handle assembly 10. The membrane 62 is of the type which reseals upon withdrawal of the shape imparting element to inhibit the ingress of fluids into the interior of the handle assembly 10.

The guide member 58 and the adaptor 60 define grooves 64 and 66 (FIGS. 3 and 5), respectively, in which a distal portion of a proximal part of an electrical lead, a distal part of which forms the electrode sheath, as will be described in greater detail below, is received with the proximal part passing through the holder 12 to exit through an opening, or slot, 76 (FIG. 3) at the proximal end 18 of the holder 12. The groove 64 opens into a central bore 67 defined through the electrode sheath carrier 14 at a junction 64.1, as shown in FIG. 6 of the drawings. A proximal end of the bore 67 is occluded by the membrane 62 as shown most clearly in FIG. 5 of the drawings.

The adaptor 60 also defines a socket 69 (FIG. 5) into which a distal end of an irrigation tube (not shown) is inserted to be in fluid communication with the bore 67 of the electrode sheath carrier 14. The irrigation tube also passes through the interior of the holder 12 and exits the holder 12 through the opening 76.

Further, it is to be noted in FIGS. 3-6 of the drawings that a proximal end of the guide member 58 has a funnel-shaped opening 70 that aids in inserting the shape imparting element through the guide member 58 to exit the electrode sheath carrier 14.

A secondary guide tube 72 extends proximally from the electrode sheath carrier 14. In the case where the adaptor 60 is provided, the secondary guide tube 72 extends from a proximal side of the adaptor 60. In the case where the adaptor 60 is omitted, the tube 72 is mounted to a proximal end of the guide member 58.

The tube 72 is slidably received over the primary guide tube 36 to assist in maintaining accurate axial displacement of the electrode sheath carrier 14 relative to the distal portion 40 of the tubular part 30 of the slide 20 as the electrode sheath carrier 14 is displaced axially relative to the slide 20.

In an embodiment, the handle assembly 10 is intended for use with a shape imparting element in the form of a steering shaft. The steering shaft is omitted from the drawings. The steering shaft is of the type having an outer tubular element and an inner actuator received in a passage of the tubular member. The actuator and the tubular member are fast with each other at a connection at a distal region of the steering shaft. The tubular member defines a bend-enhancing region proximally of the connection of the tubular member and the actuator so that when there is relative axial displacement between the tubular member and the actuator occurs, bending of the tubular member about the bend-enhancing region occurs. The steering shaft is described in greater detail in the Applicant's International Patent Application No. PCT/AU2005/000216, dated Feb. 18, 2005 and titled "A Steerable Catheter."

Figure 1:
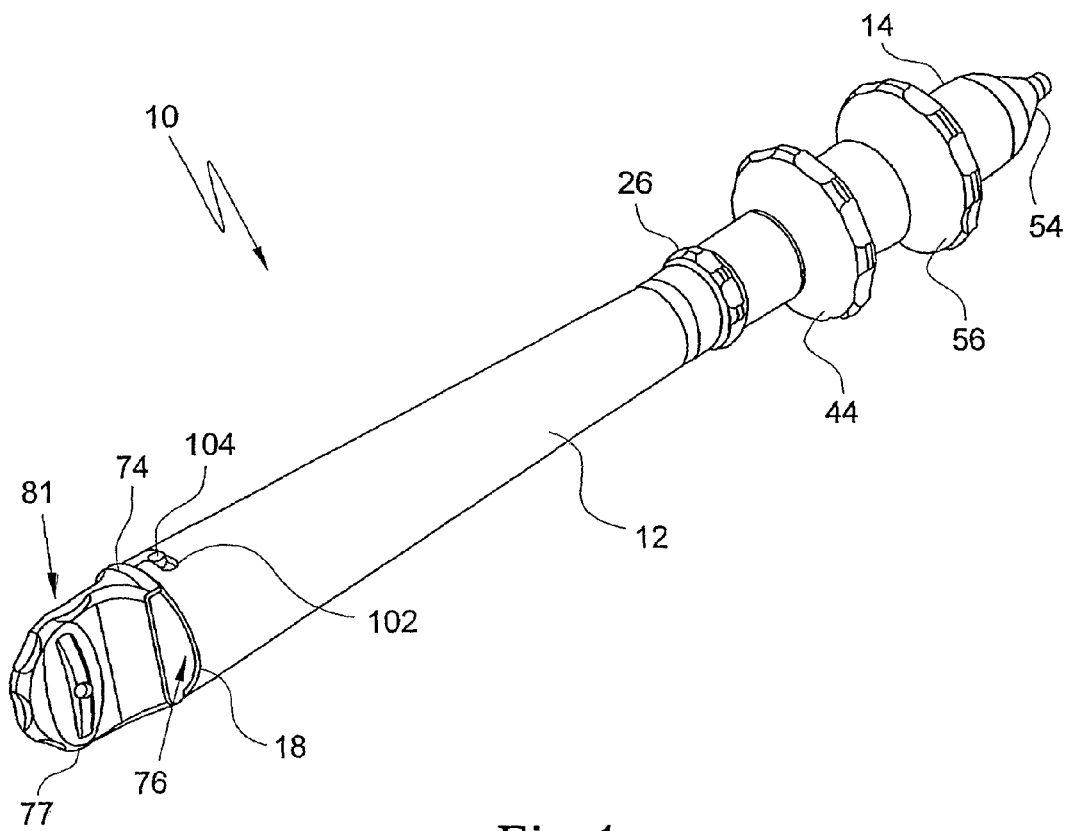
FIG. 1 shows a three-dimensional, rear view of a catheter handle assembly, in accordance with an embodiment of the invention.
Figure 7:
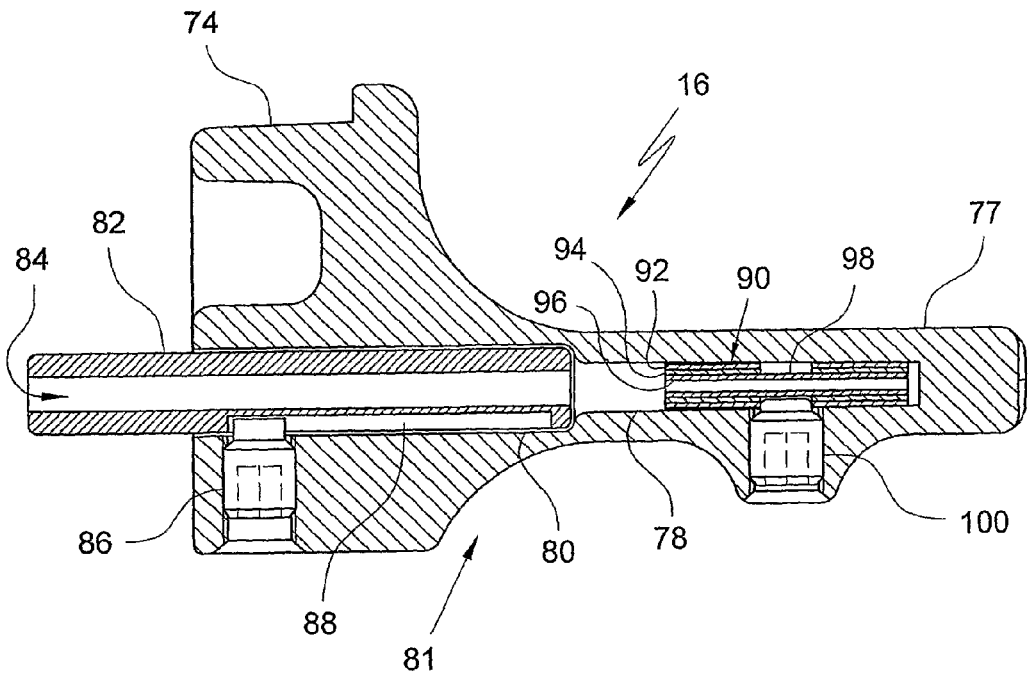
FIG. 7 shows a sectional plan view of a shape imparting element carrier of the handle assembly.

Referring to FIG. 7 of the drawings, the knob 16 is described in greater detail. The knob 16 has a boss 74 which is received in the proximal end 18 of the holder 12 and is generally shaped to be a snug fit within the proximal end 18 of the holder 12. However, as shown most clearly in FIG. 1 of the drawings, a part of the boss 74 is cut away to define the access opening or slot 76 through which the electrical lead (described in greater detail below with reference to FIG. 8 of the drawings) and the irrigation tube, if applicable, pass.

A paddle-shaped handle 77 projects proximally from the boss 74. The paddle-shaped handle 77 defines a passage 78 opening out into a wider passage 80 in the boss 74. The boss 74 and the handle 77 together form a manipulating element 81.

A receiving member 82 which receives the outer, tubular member of the steering shaft is axially, slidably received in the passage 80 of the manipulating element 81. The receiving member 82 defines a bore 84 within which the tubular member of the steering shaft fits snugly. The receiving member 82 is held slidably captive in the passage 80 by means of a grub screw 86 which is received through the boss 74 into an axially extending, blind groove 88 defined in a side of the receiving member 82. As shown more clearly in FIGS. 2 to 4 of the drawings, the receiving member 82 is of polygonal, more particularly, square cross-section, to inhibit rotation of the receiving member 82 relative to the manipulating element 81. Accordingly, the passage 80 is of a corresponding polygonal cross-section.

Packing 90, in the form of a plurality of nested tubes 92, 94 and 96, is arranged in the passage 78 and receives the actuator of the steering shaft therein. It is to be noted that, if desired, the packing 90 can be omitted or can be of fewer tubes to accommodate the actuator of the steering shaft. The packing 90 defines an annular groove 98 in which a grub screw 100 is received for locking the actuator of the steering shaft to the manipulating element 81.

The proximal end 18 of the holder 12 has a pair of opposed receiving formations, each in the form of an L-shaped slot 102. One of the slots 102 is shown more clearly in FIGS. 1 and 2 of the drawings. The manipulating element 81 has a pair of opposed locating formations, in the form of opposed radially outwardly extending pins 104. The pins 104 are received in the slots 102 and, by turning the manipulating element 81 through a predetermined arc after insertion of the pins 104, the manipulating element 81 is locked to the proximal end 18 of the holder 12.

Similarly, as shown in greater detail in FIG. 4 of the drawings, a proximal end of the body member 28 of the slide 20 has a pair of opposed receiving formations each of which, once again, is in the form of an L-shaped slot 106. One of the slots 106 is shown in more clearly in FIG. 2 of the drawings.

The receiving member 82 carries, at its distal end, a pair of opposed locating formations in the form of a pair of opposed outwardly extending pins 108. The pins 108 are received in the slots 106, when the slide 20 is fully at its proximal position within the holder 12. This locks the receiving member 82 to the slide 20 to move with the slide 20 as the slide 20 is displaced under the action of the slide control member 44. As described in greater detail in the Applicant's International Patent Application No. PCT/AU2005/000216, referred to above, when the actuator of the steering shaft and the tubular element of the steering shaft are moved relative to each other, a bending action is effected at a distal end of the steering shaft. Thus, by relative movement between the receiving member 82 and the manipulating element 81 under the effect of the slide 20, this bending action is achieved.

The proximal friction pad 52 has a tab 110 (FIG. 4) projecting from an operatively lower surface to be received in a groove 112 in the proximal portion 38 of the tubular part 30 of the slide 20. The friction pad 52 is located in position by a grub screw 114 and also locates the slide 20 relative to the holder 12.

Similarly, the distal friction pad 52 has a tab 116 on its lower surface which is received in a groove 118 in the distal portion 40 of the tubular part 30 of the slide 20. The distal friction pad 52 is secured relative to the electrode sheath carrier 14 via a grub screw 120 and also locates the electrode sheath carrier 14 relative to the distal portion 40 of the tubular part 30 of the slide 20. It will be appreciated that, with this arrangement, axial sliding movement of the slide 20 relative to the holder 12 is effected and, similarly, axial sliding movement of the electrode sheath carrier 14 relative to the slide 12 is effected. These frictionally restricted movements are governed by the friction pads 52.

It is intended that the handle assembly 10 will, largely, be a one-use device which will be disposed of. However, the knob 16 comprising the manipulating element 81 and the receiving member 82 are reused. Thus, the manipulating element 81 is of a sterilizable or heat resistant plastics material or a metal, such as titanium or stainless steel, while the receiving member 82 is of a metal which can be heat treated. The knob 16 and the receiving member 82 are re-used while the remainder of the handle assembly 10 is disposed of after a single use.

Figure 8:
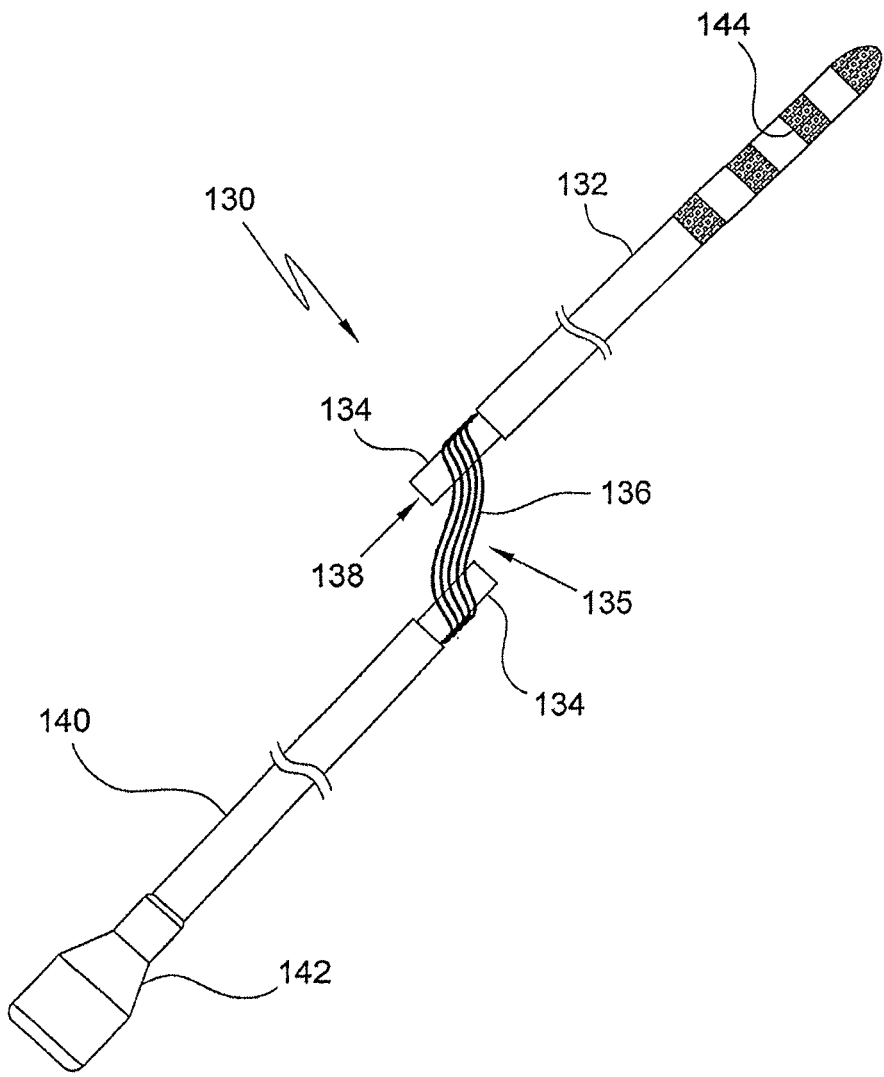
FIG. 8 shows a schematic representation of an electrical lead, in accordance with another embodiment of the invention.

Referring now to FIG. 8 of the drawings, an embodiment of an electrical lead is illustrated and is designated generally by the reference numeral 130. The electrical lead 130 is substantially greater in length than the length of electrode sheath required for use as a catheter. The electrical lead 130 has a distal part 132 which is of the requisite length and forms the electrode sheath of the catheter. Conductors 136 are wound around the lumen defining member 134, for normal use. At a proximal end of the electrode sheath portion 132, a lumen defining member 134 of the electrical lead is accessed by unwinding the conductors 136 from the lumen defining member 134. By unwinding the conductors 136 and separating the lumen defining member 134 to form a discontinuity 135 in the lumen defining member 134, access can be gained to a lumen 138 of the lumen defining member 134 of the distal part 132. A proximal end of the distal part 132 is, in use, secured to a distal end of the electrode sheath carrier 14.

The remaining, proximal part 140 of the electrical lead 130, with its conductors 136 wound about it, forms an electrical cable of the catheter and passes via the grooves 64 and 66 of the guide member 58 and the adaptor 60, respectively, and passes internally through the holder 12 to exit through the slot 76 defined between the manipulating element 81 and the proximal end 18 of the holder 12. An electrical connector 142 is connected to the proximal end of the proximal part 140 of the electrical lead 130 for connection to a patient cable or other equipment (not shown).

It will be noted that a distal end of the distal part 132 of the electrical lead 130 carries electrodes 144 thereon. Further, due to the construction of the guide member 58 and, optionally, the adaptor 60, when the electrode sheath carrier 14 is displaced relative to the slide 20, the entire electrical lead 130 moves together with the electrode sheath carrier 14.

It is a particular advantage of the invention that a handle assembly 10 is provided which is ergonomically sound and balanced to provide ease of use for a clinician. It is a further advantage of the invention that a handle assembly 10 is provided, which facilitates the passage of conductors and/or irrigation tubes internally through the handle assembly 10. Thus, the likelihood of these cables and/or irrigation tubes getting in the way are reduced. This is facilitated by the construction of the electrical lead 130.

It is still a further advantage of the invention that a handle assembly 10 is provided which has a reusable part thereby reducing costs and minimizing damage to the environment. In this regard, it is to be noted that the holder 12, the electrode sheath carrier 14 and the slide 20 are low-cost items that can be disposed of after one use and, if possible, can be recycled. These parts do not carry any electrically conductive material therein. This facilitates disposal of these parts and their recycling.

In addition, the absence of an electrical connector at the distal end of the handle assembly 10 facilitates insertion of the shape imparting element into the lumen-defining part 134 of the electrical lead 130 attached to the electrode sheath carrier 14. The ease of insertion of the shape imparting element is further facilitated by the construction of the proximal part of the slide 20 and the guide member 58 of the electrode sheath carrier 14.

Still further, the facility of having the electrode sheath displaceable relative to the shape imparting element assists a clinician to position the electrodes at hard to reach locations at a site in the patient's body and/or to improve tissue/electrode contact at the site. The fact that the part of the electrical lead 130 within the holder 12 moves with electrode sheath carrier 14 improves the ease of use of the handle assembly 10.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A catheter handle assembly, comprising:
a holder having a proximal end and a distal end, the holder configured to be gripped by a user's hand;
an electrode sheath carrier arranged at the distal end of the holder;
a shape-imparting element carrier repeatably mountable to and detachable from the proximal end of the holder, the shape-imparting element carrier having at least one mounting formation, the at least one mounting formation configured to mount at least a part of a shape-imparting element; and
a slide displaceably arranged in the holder with a distal end of the slide mounting the electrode sheath carrier and a proximal end of the slide terminating in proximity to a distal end of the shape-imparting element carrier.

2. The catheter handle assembly of claim 1, wherein the holder tapers inwardly from its proximal end to its distal end.

3. The catheter handle assembly of claim 1, wherein an abutment is arranged on the holder to provide a grip for a user's hand.

4. The catheter handle assembly of claim 1, further comprising a shape-imparting element, wherein the shape-imparting element carrier comprises a manipulating element and a receiving member, the receiving member configured for receiving a further part of the shape-imparting element, the receiving member slidably received in an end of the manipulating element.

5. The catheter handle assembly of claim 4, wherein the manipulating element and the receiving member include locating formations receivable in complementary receiving formations of the holder and the slide, respectively.

6. The catheter handle assembly of claim 5, wherein the slide includes a guide arrangement arranged in proximity to the receiving formation of the slide, the guide arrangement guiding the shape-imparting element into a proximal end of the slide.

7. The catheter handle assembly of claim 6, wherein the slide includes a body member which supports a guide member extending distally from the guide arrangement.

8. The catheter handle assembly of claim 7, wherein a secondary guide member extends proximally from the electrode sheath carrier, the secondary guide member cooperating with the guide member of the slide for guiding and supporting the shape-imparting element in the holder.

9. The catheter handle assembly of claim 7, wherein a distal part of the body member includes a tubular part and projects from the distal end of the holder, the electrode sheath carrier being slidably received on a distal portion of the tubular part.

10. The catheter handle assembly of claim 9, wherein the tubular part includes a proximal portion arranged in the distal end of the holder, the proximal portion being separated from the distal portion by a mount, a slide control member being carried by the mount.

11. The catheter handle assembly of claim 10, wherein the proximal portion and the distal portion of the tubular part each carry a friction-inducing component for increasing friction between the slide and the holder and between the slide and the electrode sheath carrier, respectively.

12. The catheter handle assembly of claim 1, wherein the electrode sheath carrier carries a guide element that facilitates insertion of the shape-imparting element through the electrode sheath carrier.

13. The catheter handle assembly of claim 12, wherein the electrode sheath carrier includes an adaptor carrying a closure element for inhibiting backflow of fluid into the holder.

14. The catheter handle assembly of claim 4, wherein the manipulating element has a substantially paddle-shaped handle projecting axially from the holder.

15. The catheter handle assembly of claim 14, wherein the proximal end of the holder and the manipulating element define an access opening through which at least one of a bundle of electrical conductors and a conduit can pass.

* * * * *